Figure 1:
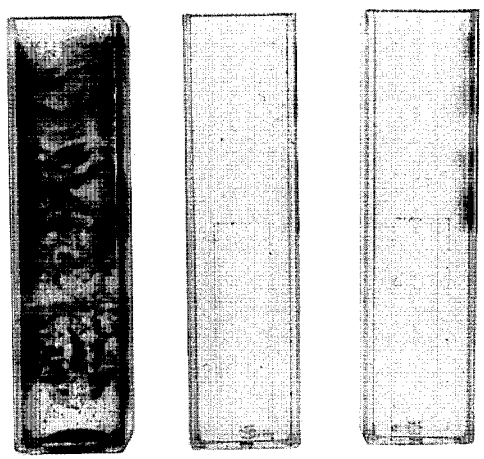

United States Patent [19]

Weiss et al.

[11] Patent Number: 4,525,342
[45] Date of Patent: Jun. 25, 1985

[54] DENTAL AND ORAL PREPARATION

[76] Inventors: Ervin Weiss, 18 Kley St., Tel Aviv; Melvin Rosenberg, 12 Yeda-am St., Ramat-gan; Herbert Judas, 5 Habrosh St., Raanana, all of Israel

[21] Appl. No.: 582,065

[22] Filed: Feb. 21, 1984

[30] Foreign Application Priority Data

Mar. 3, 1983 [IL] Israel ........................................ 68027

[51] Int. Cl.³ ............................. A61J 7/00; A61J 7/16
[52] U.S. Cl. ........................................ 424/49; 222/94; 222/129.4; 222/192
[58] Field of Search .................................. 424/49–58; 222/94, 129.4, 192, 478, 565, 566

[56] References Cited

U.S. PATENT DOCUMENTS

| 129,469 | 7/1872 | Gaddy | 424/58 |
|---|---|---|---|
| 428,033 | 5/1890 | Alson | 424/58 |
| 624,925 | 5/1899 | Grapewine | 424/58 |
| 1,645,791 | 10/1927 | Brownlee | 424/49 |
| 1,916,403 | 7/1933 | Atkinson | 424/58 |
| 1,933,977 | 11/1933 | Harris | 424/49 |
| 2,089,845 | 8/1937 | Atkins | 424/49 |
| 2,090,437 | 8/1937 | Woldman | 424/53 |
| 2,994,642 | 8/1961 | Bossard | 424/44 |
| 3,475,533 | 10/1969 | Maryrand | 424/57 |
| 3,574,824 | 4/1971 | Echeandia et al. | 424/50 |
| 3,876,759 | 4/1975 | Pensak et al. | 424/58 |
| 4,071,614 | 1/1978 | Grimm | 424/58 |
| 4,169,885 | 10/1979 | Raaf et al. | 424/52 |
| 4,348,378 | 9/1982 | Kosti | 424/49 |
| 4,411,885 | 10/1983 | Barels et al. | 424/49 |

FOREIGN PATENT DOCUMENTS

| 1959275 | 5/1971 | Fed. Rep. of Germany | 424/58 |
|---|---|---|---|
| 2426916 | 1/1976 | Fed. Rep. of Germany | 424/58 |
| 2207705 | 6/1974 | France | 424/155 |
| 54-44043 | 4/1979 | Japan | 424/58 |
| WO80/02371 | 11/1980 | PCT Int'l Appl. | 424/49 |
| 1429774 | 3/1976 | United Kingdom | 424/49 |

OTHER PUBLICATIONS

Jacobs American Perfumer & Essential Oil Review 61 (5): 389391393, May 1953, How to Flavor Toothpaste.
Jacobs American Perfumer & Essential Oil Review 61 (6): 469–471, Jun. 1953, Flavoring Mouthwashes.
Arctander (1969), Perfume & Flavor Chemicals(II) D–Limonene "Citrus Terpenes".
Derfer C.A. 68 #81372b (1968), Derfer C.A. 59, #11185B (1963), Turpentine, Flavors from.
Yousef C.A. 91 #151896b (1979), Antimicrobial Activity of Volatile Oil Components (Limonene).
Morris et al., C.A. 91 #134706x (1979), Antimicrobial Activity of Aroma Chemicals and Essential Oils.

Primary Examiner—Shep K. Rose
Attorney, Agent, or Firm—Bucknam and Archer

[57] ABSTRACT

There are provided compositions for dental and oral hygiene which desorb microorganisms and which adsorb odorous mercapto-compounds which cause halitosis. The compositions comprise as active ingredient hydrophobic materials selected from vegetable oils, certain mineral oils and hydrocarbons.

5 Claims, 2 Drawing Figures

DENTAL AND ORAL PREPARATION

FIELD OF THE INVENTION

The invention relates to novel compositions for removing bacteria and other microorganisms from the oral cavity, and especially from the surface of teeth, and removing odor producing materials from oral cavity. The compositions are based on hydrophobic constituents which desorb microorganisms from teeth and other surfaces. The compositions are provided as toothpastes, gels, mouthwash, etc.

BACKGROUND OF THE INVENTION

Tooth decay and periodontal disease are due to bacterial accumulations on the surfaces of teeth in the form of a macroscopic layer generally referred to as dental plaque. Generation of dental caries (cariogenesis) is linked to the presence of certain types of bacteria on the surfaces of teeth. Marginal gingivitis and also certain cases of halitosis have been attributed to the presence and activity of bacteria in the oral cavity.

The most widely practiced treatment of teeth is by brushing with a toothbrush, using certain dentifrices. These generally contain abrasives and detergents. By the mechanical and abrasive action dental plaque is removed from the surfaces of teeth and from crevices. The efficacy of conventional dentrifices is due to the action of the abrasive components and of the detergent ingredients. Such dentifrices may also contain substances such as fluorides and antibacterial agents. The detergents cause foaming, which gives the user a psychological feeling of cleaning action. The use of detergents in the oral cavity also has adverse effects, amongst which there have been reported: gum recession, circulatory impairment, hyperhydration of the exposed tissue, edema, as well as allergic reactions. Detergents are apt to cause stratum corneum swelling, separation between cells as well as increased permeability of human epidermis. It is apparent that the use of less harsh means ought to have an overall beneficial effect.

SUMMARY OF THE INVENTION

There are provided compositions for the removal of microorganisms and especially of bacteria from the oral cavity and from the surface of teeth. The compositions are also effective in the removal of odor-forming constituents and thus for the alleviation of or removal of the effects of halitosis. The compositions contain an active ingredient which removes the microorganisms from surfaces to which they are attached, and which absorb hydrophobic sulfide compounds which cause halitosis. The effective constituent is of a highly hydrophobic nature and a high percentage of adherent oral isolates (about 72 percent) were found to bend avidly to hydrophobic liquids, such as hexadecane, to certain natural oils and the like. As most oral bacteria present in dental plaque and saliva possess pronounced cell surface hydrophobicity, it is possible to effectively remove them by contacting the same with a composition containing such hydrophobic constituent as active ingredient. Amongst active ingredients in the compositions of the invention, there are to be mentioned various types of physiologically acceptable hydrocarbons, vegetable oils and mineral oils. Thus, there are provided according to the invention essentially detergent-free compositions for dental hygiene, such as toothpastes, mouthwashes, and the like, which are based on such oily substances, adapted to effectively desorb, and thus remove, microorganisms from the oral cavity and especially from the surface of teeth.

Experiments have shown that the above defined compounds are also effective for the removal of the unpleasant odor from saliva samples which were allowed to putrify. The odor of halitosis is effectively removed by the compositions of the invention.

The active ingredients of the novel preparations are hydrocarbons and/or fats and/or oils, if desired in combination with aqueous media, or essential oil with antibacterial activity, sweetener, cosmetic additives, preservative, food color and additive such as fluoride or the like. The dentifrice may comprise two phases, an oily one, and an aqueous one, to be mixed just prior to their use.

The high effectivity of hydrocarbons and/or oils of various origin to desorb and bind microorganisms, and especially bacteria of dental plaque, is demonstrated by the following test results.

The compositions of the invention can be effectively used for irrigation of the oral cavity. They can be used for application with irrigation devices such as Water-Pik or the like. The compositions may contain a bacteriostatic or bactericidal agent.

Experiments were carried out in which the ability of the surfaces of teeth to bind hydrophobic bacteria was established. A hydrophobic non-oral bacterium, *Acinetobacter calcoaceticus* RAG-1 (ATCC 31012) and its nonhydrophobic mutant, MR-481 were compared for their adherence to extracted teeth and to human teeth in situ. The hydrophobic RAG-1 cells adhered avidly to the surface of the teeth whereas the MR-481 cells were deficient in their ability to attach to same.

The results presented in Table 1 demonstrate the high effectivity of certain oils in binding bacteria obtained directly from dental surfaces. Amongst oils with a high degree of effectivity there may be mentioned purified olive oil, corn oil and certain hydrocarbons, such as hexadecane and the like.

Experiments were also carried out with test surfaces, such as polystyrene, to which bacteria were bound, and from which these were removed by contacting same with compositions containing as active ingredient olive oil, corn oil or hydrocarbons, such as hexadecane. The high effectivity of removal was established by various techniques, such as staining and by comparing the growth of microorganisms remaining on the test surface after tretment (FIGS. 1 and 2; Tables 1 and 2

TABLE 1

Adherence of dispersed plaque to hydrocarbons[a]

| Oil | % adherence following[b] | |
|---|---|---|
| | 1st extraction | 2nd extraction |
| hexadecane | 23 | 78 |
| octane | 51 | 87 |
| xylene | 73 | 100 |
| olive oil | 48 | 73 |

[a]Supragingival dental plaque was collected from a single individual, dispersed by sonic oscillation, washed twice and suspended in saline to yield an initial absorbance of ca. 1.0 at 400 nm, as measured by a Gilford 240 Spectrophotometer. To 1.2 ml of dispersed plaque 0.3 ml of hydrocarbon or olive oil were added and the mixtures mixed uniformly for 120 sec. Following phase separation, absorbance of the lower aqueous phase was measured. The lower aqueous phase was then transferred to a fresh test tube, an additional 0.3 ml of hydrocarbon or olive oil were added, and the phases were again mixed as previously. Following this second extraction, the lower aqueous phase was again removed, and its absorbance recorded.
[b]Results are presented as the percentage decrease in absorbance, compared with that of a sample mixed in the absence of added hydrocarbon or olive oil.

TABLE 2

Desorption of *Acinetobacter calcoaceticus* from polystyrene test tubes by n-alkane

| Alkane | Absorbance (arbitrary units) |
| --- | --- |
| control (washed in buffer alone) | 100 |
| octane | 102 |
| decane | 103 |
| tetradecane | 17 |
| hexadecane | 8 |

TABLE 3

Desorption of *Acinetobacter calcoaceticus* from polystyrene test tubes by edible oils

| Oil | Absorbance (arbitrary units) |
| --- | --- |
| control (washed in buffer alone) | 100 |
| Safflower seed oil | 51 |
| Soybean oil | 39 |
| Olive oil | 33 |
| Coconut oil | 15 |

Legend to Tables 2 and 3: RAG-1 cells were grown overnight to stationary phase in brain heart infusion broth, washed twice and suspended in PUM buffer. One ml of bacterial suspension was added to polystyrene test tubes which were incubated overnight at 37 C. The test tubes were washed twice with PUM to remove nonadherent bacteria. To 1.5 ml PUM buffer in each test tube, 0.3 ml of n-alkane (Table 2) or oil (Table 3) were added and the test tubes vortexed under controlled conditions for 8 min. Following this washing procedure, the mixtures were poured off from the test tubes and the test tubes were washed four times with PUM buffer. Adherent cells were then fixed with methanol and stained with Gentian Violet. Absorbance was measured in a Payton aggregometer fitted with a red filter. Vegetable oils were obtained from Sigma.

Desorption was studied by simple techniques: *Acinetobacter calcoaceticus* RAG-1 (ATCC 31012) cells were grown 18 h to stationary phase in brain heart infusion broth (Difco), conditions which optimize their adherence characteristics. Cells were harvested, washed twice and suspended in PUM buffer (22.2 g $K_2HPO_4.3H_2O$; 7.26 $KH_2PO_4$; 1.8 g urea, 0.2 g $MgSO_4.7H_2O$ and distilled water to 1000 ml, pH 7.1), to a turbidity of ca. 250 Klett units (measured in a Klett Summerson colorimeter fitted with a green filter). In order to obtain a layer of bound cells, 1.5 ml cell suspension was mixed by vortex for 60 seconds within standard polystyrene cuvettes (Rudolph Brand, Wertheim/Main, FRG). The cell suspension was then poured from the cuvettes. Each cuvette was then washed with 1.5 ml PUM to remove non-bound or poorly attached cells.

To 1.5 ml PUM in each cell-coated cuvette, 0.3 ml olive oil or hexadecane were added, and the mixtures were agitated for 120 seconds by hand. The mixtures were poured off and the process repeated. Following the second mixing, cuvettes were rinsed four times with 1.5 ml PUM to remove as much of the non-aqueous phase as possible from the cuvettes. Control cuvettes were subjected to exactly the same treatment, except that the mixing was performed with 1.5 ml PUM, in the absence of oil.

In order to study desorption of cells qualitatively, cuvettes were fixed with methanol and stained with Gentian Violet. As seen in FIG. 1, control cuvettes which were washed in the absence of oil maintained a dense layer of attached RAG-1 cells, despite the repeating mixings in the presence of buffer. However, cuvettes washed in the presence of either olive oil or hexadecane appeared completely free of bound cells.

In order to obtain a quantitative estimate of the number of remaining adherent cells, 1.2 ml of minimal medium consisting of PUM supplemented with 0.2% sodium acetate as carbon and energy source, was added to each cuvette. Cuvettes were incubated horizontally at 30° C. Growth was followed turbidimetrically directly in the cuvettes at 400 nm using a Uvikon 710 spectrophotometer (Kontron, Zurich, Switzerland).

Figure 2:
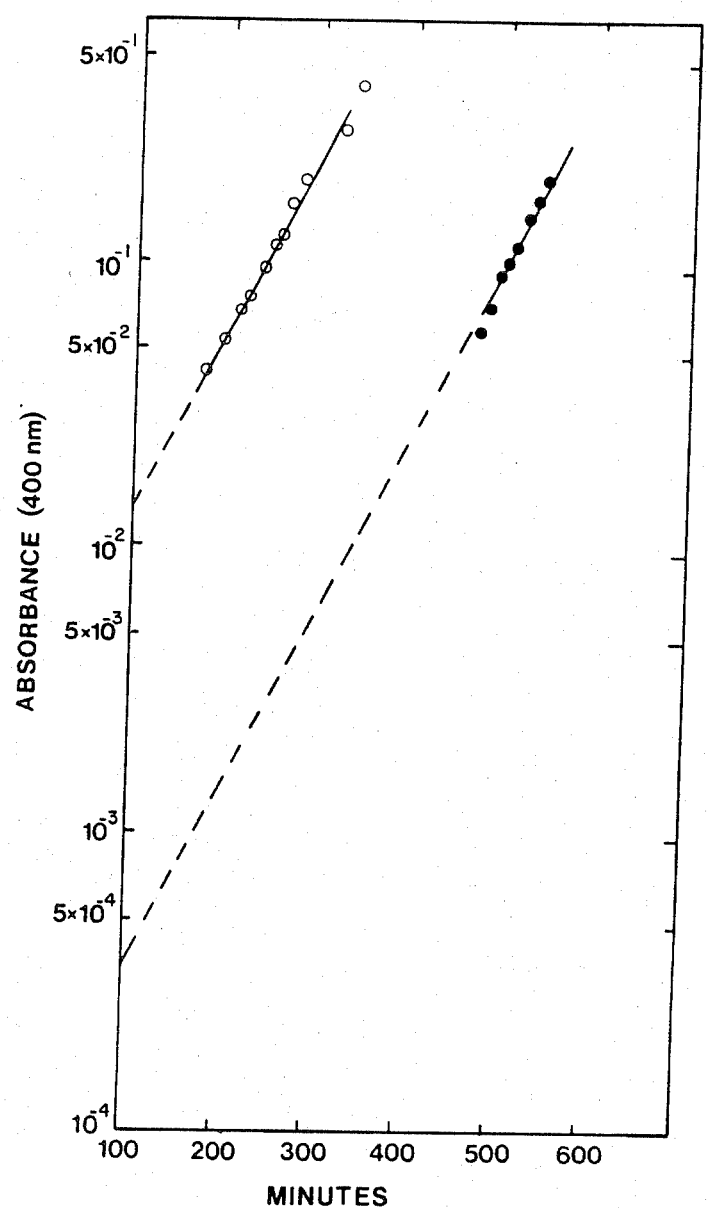

Results of a typical experiment are shown in FIG. 2. In the control cuvette, exponential growth was observed following ca. 3 h of incubation. In the cuvette washed with olive oil, growth commenced after 6 h. In both cases doubling time was observed to be the same (50 min). Since an appropriate dilution (1:200) of the RAG-1 cells used in the experiment inoculated into the minimal medium grew following a lag of 100 min (not shown), back extrapolation of the growth curves to 100 minutes provided an estimation of the initial bacterial populations. The extrapolated initial value obtained for the olive-oil washed cuvette ($3.5 \times 10^{-4}$) was approximately 2.5% of that observed for the control ($1.4 \times 10^{-2}$). Thus, at least 97% of the bound RAG-1 cells were removed from the cuvette by this procedure, as compared with the control washed in PUM alone. No growth whatsoever was observed in the hexadecane-washed cuvettes during the course of the experiment (9 h), indicating an even higher level of bacterial desorption. Following 20 h incubation, all the cuvettes reached approximately the same turbidity (0.95–1.07), indicating an equivalent growth yield. It should be emphasized that neither hexadecane nor olive oil is toxic for RAG-1 cells; both hexadecane and olive oil can serve as carbon and energy source for growth of RAG-1. The equivalent growth rates measured in the control and olive-oil washed cuvettes provide further evidence that inhibitory effects were not involved in the difference observed, but rather the initial bacterial concentration.

Quantitative comparisons of decorption ability of various n-alkanes and oils were carried out by ascertaining the level of stain remaining on RAG-1 coated test tubes which were washed by aqueous:oil mixtures. Hexadecane (Table 2) and coconut oil (Table 3) were particularly efficient in desorbing bound bacteria.

Qualitative experiments have shown the high effectivity of a mouthwash based on a mixture of 2:1 (v/v) of tap water/olive oil used for swishing the mouth. The mixture was examined and found to contain oil droplets with various forms of oral bacteria adhering to same. The treated surfaces were cleaned in a highly effective manner and only a small percentage of the initial population of microorganisms remained on the surface. Further experiments were carried out by staining dental plaque with erythrosine which specifically stains oral bacteria. Swishing with tap water removed less and less stain. When the swishing was effected with a mixture containing olive oil, a high level of dye was removed together with the plaque, which concentrated at the oil/water interface. As control an aqueous erythrosine solution was mixed with olive oil and no removal of the dye into the oily phase or at the oil/water interface was observed.

The above experiments were corroborated by quantitative clinical trials, performed with four volunteers. In these experiments, volunteers swished their mouths for seven consecutive thirty-second periods under controlled conditions. The first four swishings were performed with 7.0 ml saline. The two subsequent swishing mixtures consisted either of a 1:1 saline:oil mixture (7.0 ml final volume), or of commercial mouthwash, diluted according to manufacturer's label. The final (seventh) rinse consisted of saline alone. Each volunteer performed a single experiment (seven rinsings) per day.

The amount of biological debris (i.e., bacteria and desquamating epithelial cells) was ascertained quantitatively. Following each swishing, the mixture was expelled from the mouth into centrifuge tubes, and the exact volume recorded. Mixtures were standardized by the following procedure: in experiments comparing oil:saline with saline, the expelled saline rinses were supplemented with 3.5 ml oil, and the oil:water rinses were supplemented with 3.5 ml saline. In this manner, each tube contained ca. 7.0 ml saline+3.5 ml oil. The mixtures were shaken for two minutes. Following this, an equal volume (1 ml) of Gentian violet solution was added to each tube, to an initial concentration corresponding to 1.8-1.9 O.D. at 585 nm, as measured in a Uvikon spectrophotometer. The tubes were again mixed and then centrifuged to clarify the emulsions. Following centrifugation, stain was observed to concentrate both at the oil:aqueous interface, and in the pellet. Microscopic observation revealed that the stained material consisted almost exclusively of oral bacteria and epithelial cells bearing adherent bacteria. Control experiments with different amounts of oral debris demonstrated that a correlation exists between the amount of stain absorbed from the aqueous phase and the amount of oral debris present. The amount of stain absorbed by the oral debris was determined by measuring the concentration of stain remaining in the bulk aqueous phase. This was performed spectrophotometrically by dichromic (585 nm-625 nm) measurement of the bulk aqueous phase. Results obtained spectrophotometrically were corrected for variations in volume of the expelled rinses and expressed as the difference in optical density of the bulk aqueous phase relative to the value obtained for the first rinsing of the same experiment.

Results of the experiments in which four volunteers each performed six experiments (three with oils, three with commercial mouthwashes) is summarized in Table 4. In general, consecutive rinsings with saline (numbers 1-4 in each experiment) removed less and less oral debris, as observed in an increase in optical density of the bulk aqueous phase. However, when the saline was substituted by saline:oil mixtures, removal of higher amounts of oral debris were recorded. Best results were obtained using soya bean oil. The seventh rinse, performed with saline alone, achieved poorer results. The cleansing effect of the oils was not observed in parallel experiments performed with commercial mouthwashes.

These experiments provide direct evidence that rinsing with oil:aqueous solutions in situ has a superior effect in cleansing the oral cavity.

TABLE 4

Relative Concentration of Gentian Violet Remaining in Aqueous Phase following Centrifugation of Expelled Oral Swishes

| Volunteer No. | Swish no. | Coconut oil | Olive oil | Soya Bean oil | "Eludril" commerical mouthwash | "Tayadent" commerical mouthwash | "Listermint" commerical mouthwash |
|---|---|---|---|---|---|---|---|
| 1 | 1 | 1.0 | 1.0 | 1.0 | 1.0 | 1.0 | 1.0 |
|   | 2 | 0.98 | 1.04 | 1.28 | 1.28 | 1.10 | 1.08 |
|   | 3 | 1.07 | 1.16 | 1.38 | 1.33 | 1.10 | 1.14 |
|   | 4 | 1.11 | 1.13 | 1.30 | 1.37 | 1.13 | 1.19 |
|   | 5 | 0.74 | 0.76 | 0.41 | 1.38 | 1.71 | 1.21 |
|   | 6 | 0.75 | 0.78 | 0.35 | 1.42 | 1.44 | 1.21 |
|   | 7 | 1.06 | 1.16 | 1.49 | 1.27 | 0.97 | 1.21 |
| 2 | 1 | 1.0 | 1.0 | 1.0 | 1.0 | 1.0 | 1.0 |
|   | 2 | 1.33 | 1.38 | 1.29 | 1.32 | 1.01 | 1.11 |
|   | 3 | 1.39 | 1.41 | 1.40 | 1.38 | 1.07 | 1.08 |
|   | 4 | 1.45 | 1.51 | 1.63 | 1.49 | 1.11 | 1.15 |
|   | 5 | 1.15 | 1.11 | 0.79 | 1.63 | 1.48 | 1.10 |
|   | 6 | 1.17 | 0.84 | 0.79 | 1.62 | 1.31 | 1.12 |
|   | 7 | 1.42 | 1.20 | 1.36 | 1.48 | 1.16 | 1.03 |
| 3 | 1 | 1.0 | 1.0 | 1.0 | 1.0 | 1.0 | 1.0 |
|   | 2 | 1.35 | 1.11 | 1.05 | 1.05 | 0.99 | 1.05 |
|   | 3 | 1.47 | 1.07 | 1.10 | 1.08 | 1.02 | 1.01 |
|   | 4 | 1.50 | 1.38 | 1.10 | 1.16 | 1.08 | 1.12 |
|   | 5 | 1.29 | 0.98 | 0.75 | 1.30 | 1.54 | 1.09 |
|   | 6 | 1.22 | 0.98 | 0.67 | 1.25 | 1.39 | 1.08 |
|   | 7 | 1.43 | 1.30 | 0.85 | 1.11 | 1.11 | 1.11 |
| 4 | 1 | 1.0 | 1.0 | 1.0 | 1.0 | 1.0 | 1.0 |
|   | 2 | 1.17 | 1.16 | 1.26 | 1.15 | 1.05 | 1.17 |
|   | 3 | 1.22 | 1.13 | 1.30 | 1.25 | 1.07 | 1.16 |
|   | 4 | 1.22 | 1.26 | 1.32 | 1.29 | 1.13 | 1.24 |
|   | 5 | 0.96 | 0.98 | 0.62 | 1.46 | 1.47 | 1.20 |
|   | 6 | 0.92 | 0.86 | 0.43 | 1.45 | 1.32 | 1.32 |
|   | 7 | 1.22 | 1.24 | 1.02 | 1.22 | 1.09 | 1.20 |

The oily, hydrophobic phase has a two-fold effect: desorption of microorganisms and adsorption of sulfur-containing odorous compounds, such as mercaptans which form by the action of bacteria on salivary proteins.

The novel composition can be applied by squirting into the mouth, swishing around for a while and ejection; they may be applied by means of a toothbrush, which enhances the effect by adding the mechanical effect of plaque removal.

Further experiments demonstrated the ability of hydrocarbns and different oils to remove odor producing materials from the oral cavity. Halitosis in vivo is caused mainly by stasis of saliva in different microniches in the oral cavity especially during the night, resulting in production of odorous sulphides e.g. methyl mercaptan, dimethyl sulphide, ethyl mercaptan.

In a typical experiment saliva was collected from a volunteer and equally divided in two test tubes. One ml of soybean oil was added to one of the test tubes and both were equally mixed for 60 seconds. Following phase separation the lower aqueous phase from the experiment test tube was transferred to a fresh test tube. The experimental fresh test tube and the control were incubated in 37° C. for 24 hours allowing the saliva to putrify.

Putrified saliva samples were then diluted 1:10 in P.B.S. (phosphate Buffered Salin) and examined organoleptically by five independent volunteers. All the examiners claimed of definite difference between the experimental sample and the control. The saliva sample that was mixed with oil prior to incubation exhibited slight or no unpleasant odor while the control sample had a strong foul odor. In an additional experiment, collected saliva was first allowed to putrify under the same conditions. One half of the saliva volume was mixed for 60 seconds in the presence of soybean oil and the other half served as control. Following phase separation the lower aqueous phase was transferred to a new test tube. Similar volumes of the experimental and the control samples were diluted 1:10 with P.B.S. and again examined organoleptically by five independent volunteers.

Slight or no odor was reported when smelling the experimental sample while strong foul odor was smelled form the control sample.

The following examples are intended to illustrate the invention, and these are to be construed in a non-limitative manner.

In the following examples percentages are by weight. The compositions were prepared by conventional techniques which do not require any detailed description.

| Example 1 - High viscosity mouthwash | |
|---|---|
| Olive oil | 52% |
| Coconut oil | 9.9% |
| Corn oil | 35% |
| BHTA (anti-oxidant) | 0.1% |
| Orange oil | 3% |
| Example 2 - Vitamin containing toothpaste | |
| White mineral oil | 36.0% |
| Olive oil | 33.0% |
| Coconut oil | 12.0% |
| Talc | 18.0% |
| Orange Oil | 0.9% |
| Vitamin A | .01% |
| Vitamin D$_3$ | .01% |
| Vitamin E | .1% |
| Example 3 - Low viscosity mouthwash | |
| Decane | 28.9% |
| Dodecane | 38.0% |
| Orange terpenes | 5.0% |
| Low MW silicon oil | 27.0% |
| BHTA | 0.1% |
| Orange oil | 1.0% |
| Example 4 - Toothpaste | |
| Talc | 10% |
| Kaolin | 13% |
| Beeswax | 8% |
| Carnauba wax | 3% |
| White mineral oil | 43% |
| Olive Oil | 19% |
| Anise oil | 2% |
| Cocoa butter | 1.8% |
| Pigment red 57 | 0.2% |
| Example 5 - Abrasive-free Lotion for Toothbrushing | |
| Ethyl cellulose | 9.5% |
| Mineral oil | 40.0% |
| Olive oil | 40.0% |

| -continued | |
|---|---|
| Orange terpenes | 5.0% |
| BHTA | 0.1% |
| Beta carotene | 0.2% |
| Saccharin | 0.2% |

Example 6 - Two color biphasic combination toothpaste (1:1 ratio) containing fluoride

| Oil phase: | | Water phase: | |
|---|---|---|---|
| white mineral oil | 20% | alginate | 10.0% |
| Olive oil | 20% | Saccharin | 0.2% |
| Beeswax | 35% | Water | 88.8% |
| Talc | 10% | Sodium mono- | 0.5% |
| Corn oil | 13% | fluorophosphate | |
| Lemon oil | 1.8% | erythrosine | 0.5% |
| Beta carotene | 0.2% | | |

EXAMPLE 7

A two-phase mouthwash was prepared comprising an aqueous 0.85% solution of sodium chloride in water and half the volume of oily phase: soya bean oil.

The composition was provided in a double-compartment double-squirt bottle and allowed the squirting of a small quantity (a few milliliters) of the mixture of the two ingredients into the oral cavity.

Results indicate that the composition is effective in removing dental plaque, a large percentage of adhering microorganisms and that it also reduced to a large extent halitosis.

LEGENDS TO THE FIGURES

FIG. 1: Cuvettes were washed and rinsed, as described in the test. The remaining adherent cells were visualized by fixation in methanol and staining with Gentian Violet. Left-control cuvette, washed with PUM alone; Center-cuvette washed with olive oil; right-cuvette washed with n-hexadecane.

FIG. 2: RAG-1 cells bound to polystyrene were desorbed and rinsed as described in the text. To each cuvette, 1.2 ml acetate medium (PUM supplemented with 0.2% acetate) was added. Outgrowth of cells was measured turbidimetrically. Results are back extrapolated back to the end of the lag period (100 min). (0), washed with olive oil:PUM mixture; (0), washed with PUM alone.

We claim:

1. A mouthwash for dental and oral hygiene, adapted to desorb microorganisms and absorb odorous mercapto compounds causing halitosis, which mouthwash comprises a system of two physically separate liquid phases, provided in a double compartment doublesquirt bottle adapted to be emulsified by swishing in the mouth, one of said phases being a solution of sodium chloride in water as an aqueous phase, and the other an oily phase which is a vegetable oil, a mineral oil or a hydrocarbon, said aqueous phase and said oily phase being in the ratio between 2:1 and 1:1 by volume.

2. A mouthwash according to claim 1 containing a bacteriostatic or bactericidal agent.

3. A mouthwash according to claim 1 containing also an essential oil.

4. A mouthwash according to claim 1, wherein the oily phase is a member selected from the group consisting of olive oil, corn oil, soybean oil, safflower oil, coconut oil and paraffin oil.

5. The method of removing microorganisms, odorous substances from the oral cavity which consists of irrigating the oral cavity with the mouthwash composition in accordance with claim 1 squirted as a mixture comprising an aqueous phase and an oily phase, in the ratio between 2:1 and 1:1 by volume.

* * * * *